United States Patent [19]
Wang et al.

[11] Patent Number: 5,712,386
[45] Date of Patent: *Jan. 27, 1998

[54] KITS FOR DETECTING A TARGET NUCLEIC ACID WITH BLOCKING OLIGONUCLEOTIDES

[75] Inventors: Chang-Ning J. Wang, Chelmsford; Kai-Yuan Wu, Lowell, both of Mass.

[73] Assignee: Biotronics Corporation, Lowell, Mass.

[*] Notice: The term of this patent shall not extend beyond the expiration date of Pat. No. 5,348,853.

[21] Appl. No.: 434,474

[22] Filed: May 4, 1995

Related U.S. Application Data

[60] Division of Ser. No. 250,849, May 26, 1994, Pat. No. 5,567,583, which is a continuation-in-part of Ser. No. 808,463, Dec. 16, 1991, Pat. No. 5,348,853.

[51] Int. Cl.⁶ .............................. C07H 21/04; C12P 19/34
[52] U.S. Cl. .......................... 536/24.33; 435/6; 435/91.2; 536/23.1; 536/24.3
[58] Field of Search ............ 435/6, 91.2; 536/23.1, 536/24.3, 24.33

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,725,537 | 2/1988 | Fritsch et al. | 435/6 |
| 4,800,159 | 1/1989 | Mullis et al. | 435/172.3 |
| 4,822,733 | 4/1989 | Morrison | 435/6 |
| 4,965,188 | 10/1990 | Mullis et al. | 435/6 |
| 4,996,143 | 2/1991 | Meller et al. | 435/6 |
| 5,030,852 | 7/1991 | Johnson et al. | 165/12 |
| 5,210,015 | 5/1993 | Gelfand et al. | 435/6 |
| 5,348,853 | 9/1994 | Wang et al. | 435/6 |
| 5,567,583 | 10/1996 | Wang et al. | 435/6 |

FOREIGN PATENT DOCUMENTS

| | | |
|---|---|---|
| 0200362A2 | 12/1986 | European Pat. Off. |
| 0201184A2 | 12/1986 | European Pat. Off. |
| 0236069 | 9/1987 | European Pat. Off. |
| 0320308 | 6/1989 | European Pat. Off. |
| 0333465 | 9/1989 | European Pat. Off. ......... C12K 1/68 |
| 0382433A2 | 8/1990 | European Pat. Off. |
| WO 89/09835 | 10/1989 | WIPO. |

OTHER PUBLICATIONS

Blanco, L. et al. Highly Officient DNA Synthesis by the Phage ø29 DNA Polymerase (J. Biol. Chem. (1989) 254:8935–8940.

P. Holland et al., "Detection of specific polymerase chain reaction product . . . ", Proc. Natl. Acad. Sci. USA 88:7276–7280 (1991).

G.T. Walker et al., "Isothermal in vitro amplification of DNA by a restriction enzyme/DNA polymerase system", P.N.A.S. 89:392–390 (1992).

Morrison, L. E., Halder, T.C. and Slols, L.M., "Solution-Phase Detection of Polynucleotides Using Interacting Fluorescent Labels and Competitive Hybridization", Analytical Biochemistry 183:231–244 (1989).

Primary Examiner—Kenneth R. Horlick
Attorney, Agent, or Firm—Fish & Richardson, P.C.

[57] ABSTRACT

A method for detecting a target nucleic acid, which method includes the steps of (i) amplifying the target nucleic acid to obtain an amplification product using a polymerase, a first primer with or without a segment noncontiguous to a first priming sequence, and a second primer with or without a segment noncontiguous to a second priming sequence in the presence of an oligonucleotide which is incapable of acting as a primer for the polymerase, wherein the oligonucleotide has at least 5 consecutive nucleotides fully complementary to at least 5 consecutive nucleotides of the first primer; and (ii) detecting the presence of the target nucleic acid by monitoring the amplification thereof.

18 Claims, 5 Drawing Sheets

KITS FOR DETECTING A TARGET NUCLEIC ACID WITH BLOCKING OLIGONUCLEOTIDES

CROSS REFERENCE TO RELATED APPLICATION

This is a divisional of application Ser. No. 08/250,849, filed May 26, 1994, U.S. Pat. No. 5,567,583, which is a continuation-in-part of U.S. patent application Ser. No. 07/808,463, filed Dec. 16, 1991 U.S. Pat. No. 5,348,853.

BACKGROUND OF THE INVENTION

Recent development of the polymerase chain reaction ("PCR") has provided an important tool for the detection of nucleic acid sequences present at low concentrations (Mullis, K. B. et al., U.S. Pat. Nos. 4,683,195 and 4,683,202). In PCR, a target sequence having boundaries defined by two oligonucleotide extension primers, is amplified through repeated enzymatic cycles to provide additional templates for further amplification reactions. Accordingly, a small number of target sequences can be exponentially amplified and readily detected.

A major limitation of PCR lies in the extensive generation of by-products produced as a result of non-specific priming events, e.g., random priming of the nucleic acid template and/or self priming of the extension primers. Thus, when a high number of amplification cycles are required to amplify a target sequence present at a relatively low concentration, the products of non-specific priming events significantly impede PCR sensitivity.

An additional, related limitation of PCR is the requirement for a separation step prior to detection of the amplified target. According to standard PCR conditions, separation of the amplified target sequence from the products of non-specific priming events is a prerequisite for detection of the amplified target sequence. The absence of a homogenous amplification reaction, i.e., an reaction in which amplification and detection take place in the same reaction vessel has been an obstacle in automating the PCR procedure. In addition, the requirement for a separation step also subjects the PCR mixture to potential contamination resulting from the separation procedure. The likelihood of contamination severely limits the potential application of PCR in routine clinical diagnosis.

Attempts have been reported to develop a homogeneous assay for amplification and detection. One such attempt is described by Holland et al. (1991, *Proc. Natl. Acad. Sci. USA* 88:7276, hereby incorporated by reference) in an assay utilizing the 5'→3' exonuclease activity of Taq polymerase to generate a detection signal concomitantly with PCR amplification. However, a subsequent separation step is required to detect the exonuclease generated signal. Higuchi et al. (1992, *Bio/Technology* 10: 413, hereby incorporated by reference) describes a homogeneous detection process based on monitoring enhanced fluorescence of ethidium bromide when it is intercalated into double stranded amplification product. Such a detection process is not target sequence specific, thus vulnerable to interferences from the presence of any double stranded DNA. A different approach is to use fluorescence polarization to detect hybridization of a fluorescence nucleic acid probe or fluorescence primer extension products (Garmen, A. J. et al., European Patent Office Publication No. 382,433). This detection process is able to distinguish the hybridized or extended probe, which has a higher molecular weight (thus decreased fluorescence polarization), from the unreacted probe. However, the presence of the unhybridized probe with higher polarization strongly influences the observed polarization, thus giving a high background.

Non-radiative energy transfer by close proximity of two fluorescent moieties can be used as an effective signal detection mode. Homogeneous immunoassays based on fluorescence energy transfer have been described (Patel. et. al., European Patent Application No. 137,515). Fluorescence energy transfer has also been designed for detecting nucleic acid hybridization (Heller et al., European Patent Application No., 070,685 and U.S. Pat. No. 4,996,143). In such applications, a fluorescence energy transfer signal is generated when probes carrying different fluorescent moieties are brought to the close physical vicinity as a result of hybridization to a strand of the target nucleic acid.

SUMMARY OF THE INVENTION

One aspect of this invention relates to a method for detecting a target nucleic acid, which includes the steps of: (i) amplifying the target nucleic acid to obtain an amplification product using a polymerase, a first primer with or without a segment noncontiguous to a first priming sequence, and a second primer with or without a segment noncontiguous to a second priming sequence in the presence of an oligonucleotide which is incapable of acting as a primer for the polymerase, wherein the oligonucleotide has at least 5 (preferably, at least 8) consecutive nucleotides fully complementary to at least 5 (preferably, at least 8) consecutive nucleotides of the first primer; and (ii) detecting the presence of the target nucleic acid by monitoring the amplification thereof.

The first and second primers, which correspond to a primer pair used in the PCR procedure, hybridize to the first and second priming sequences, respectively, in the target nucleic acid before being extended by the polymerase. The term "polymerase" used in this application refers to a catalyst capable of both carrying out the DNA polymerase activity and displacing a "downstream" single-stranded oligonucleotide.

The above-described oligonucleotide is a "blocking oligonucleotide" of this invention. For convenience, any oligonucleotide which (a) is incapable of being used as a PCR primer and (b) has at least 5 consecutive nucleotides fully complementary to at least 5 consecutive nucleotides of a primer (with or without a contiguous segment) is named "blocking oligonucleotide" throughout this application. A blocking oligonucleotide blocks a primer in the sense that it hybridizes with it and renders it less likely to be bound to its priming sequence in the target nucleic acid. In a preferred embodiment of this method, the amplifying step is performed in the presence of an additional blocking oligonucleotide for the second primer.

The 5-base full complementarity can form between a blocking oligonucleotide and either the contiguous segment or the noncontiguous segment of a primer. The contiguous segment of a primer is the sequence which is complementary to the priming sequence in the target nucleic acid. On the other hand, the noncontiguous segment of a primer is the sequence which is noncomplementary to the priming sequence in the target nucleic acid.

Preferred lengths of each of a primer and a blocking oligonucleotide of this invention range from 10 to 50 nucleotides (more preferably, 15–40 nucleotides.) The operative concentration of a blocking oligonucleotide varies greatly depending on several factors, e.g., degree of complementarity between a blocking oligonucleotide and its corresponding primer, assay temperature, and the like, and in any event, can be readily determined by a skilled person in the art without undue experimentation. In terms of molar ratio of a blocking nucleotide to its corresponding primer, the range 0.3–5.0 (or 0.5–2.5) is generally acceptable.

The detecting step can be performed by monitoring the amplification product of the target nucleic acid on a gel after electrophoresis. Alternatively, one can covalently attach two fluorophores to the first (or second) primer and its corresponding blocking oligonucleotide, respectively, with one of the two fluorophores being a donor fluorophore and the other being an acceptor fluorophore, so that when the first primer and the blocking oligonucleotide are hybridized, the donor fluorophore and the acceptor fluorophore are in close proximity to allow resonance energy transfer therebetween. When a blocking oligonucleotide and its corresponding primer are so fluorophore labeled, one can monitor fluorescent emission change of the acceptor fluorophore upon irradiation of the donor fluorophore with an excitation light to quantify the amplification of the target nucleic acid, since the change is a function of the extent of the blocked primer being dissociated from the blocking oligonucleotide and subsequently incorporated into the amplification product of the target nucleic acid.

Another aspect of the present invention relates to kits for detecting a target nucleic acid. For example, a detection kit of this invention can include (i) a pair of primers (10–50 bases, or 15–40 bases) to be used with a polymerase for the amplification of the target nucleic acid, each with or without a segment noncontiguous to its priming sequence; and (ii) a blocking oligonucleotide (10–50 bases or 15–40 bases) capable of blocking one of the two primers. Preferably, the blocking oligonucleotide(s) and primer(s) corresponding thereto be fluorophore labeled in a manner described above. The blocking oligonucleotide and its corresponding primer can be provided as a duplex (i.e., "specific detection duplex", see FIG. 1, middle and FIG. 2, top, and discussion below). It is also preferred that the kit further include one or both of the following reagents: a polymerase and an additional blocking oligonucleotide for blocking the other primer.

As another example, a kit of this invention can include (i) a first fluorophore labeled oligonucleotide (10–50 bases or 15–40 bases) incapable of being used as a primer in the amplification by a polymerase, and (ii) a second fluorophore labeled oligonucleotide (5–30 bases or 7–15 bases) which has a free 3' OH. Both oligonucleotides are hybridized, via at least 5 (preferably, at least 8) consecutive fully complementary nucleotide pairings, with each other, and the first oligonucleotide overhangs the 3' end of the second oligonucleotide by 1–12 bases (preferably, 4–8 bases) and further, the first and second fluorophores, one of which is a donor fluorophore and the other an acceptor fluorophore, are in close proximity to allow resonance energy transfer therebetween. The first and second oligonucleotides can be provided as a duplex, i.e., "universal detection duplex" (see discussion below). Preferably, other reagents such as a ligase, a kinase and a polymerase with or without 5'→3' exonuclease activity. Ligase and kinase (or polymerase with or without 5'→3' exonuclease activity) can be used to link any selected primer to a universal detection duplex, thereby converting the latter into a specific detection duplex.

Both the above-described specific and universal detection duplexes, as well as the "incapacitated" oligonucleotide which forms one strand of either duplex, are also within the scope of the present invention.

Other features and advantages of the present invention will be apparent from the following drawings and description of the preferred embodiments, and also from the appending claims.

BRIEF DESCRIPTION OF THE DRAWING

The drawings are first described.

DESCRIPTION OF THE PREFERRED EMBODIMENTS

Figure 1:
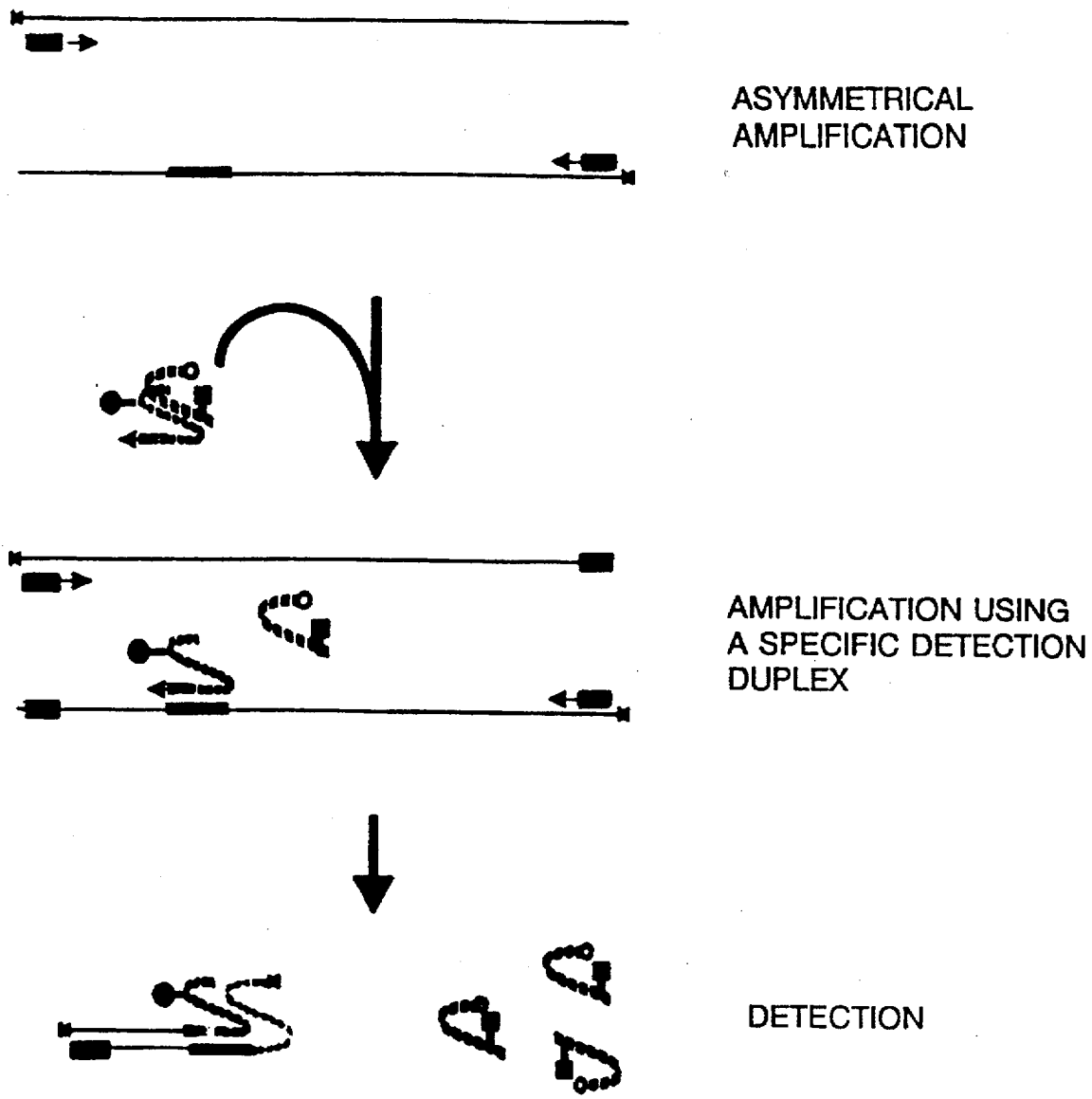
FIG. 1 is an embodiment of the method of this invention.

As used herein, "amplification" refers broadly to a process using a polymerase and a pair of primers for producing any particular nucleic acid sequence, i.e., the "target nucleic acid sequence" or "target nucleic acid," in an amount which is greater than that initially present.

The present invention relates to a method for detecting the presence of a specific nucleic acid sequence by monitoring the incorporation of the primer(s) into the amplification product of the specific nucleic acid. In the present invention, a blocking oligonucleotide is used to prevent non-specific priming events during the amplification process. In a preferred embodiment, the amplified target sequence is detected by fluorescently monitoring the dissociation of the blocking oligonucleotide from its complementary primer.

Amplification relies upon hybridization of each of a pair of primer to a specific priming sequence, i.e., a sequence of the initial nucleic acid template to which a primer has the best degree of complementarity and hybridizes most preferably. In addition to specific priming sequences, the initial nucleic acid template may include nonspecific priming sequences to which a primer may also be capable of hybridizing. Non-specific priming events, i.e., events which lead to amplification of a sequence of the template other than the specific nucleic acid sequence, include reactions such as the hybridization of a primer to a sequence of the template other than its priming sequence, and self priming such as dimerization due to inter-molecular interactions between the primers. See Chou et al. in *Nucleic Acid Research* (1992) 20:1717, hereby incorporated by reference.

A primer is an oligonucleotide, whether purified from a restriction digest or prepared by an organic method, which is capable of acting as a point of initiation of synthesis of a primer extension product complementary to a target sequence when placed under proper conditions. In addition to the sequence complementary to the specific priming sequence in the initial nucleic acid template, a primer of this invention may further encompass at its 5' region a sequence noncontiguous to the priming sequence of the initial template. In other words, a contiguous segment is a stretch of sequence at the 3' region of a primer, which sequence is complementary to the specific priming sequence in the initial nucleic acid target, whereas a noncontiguous segment is a stretch of sequence at the 5' region of a primer, which sequence is not complementary to the priming sequence of the initial nucleic acid template.

As used herein, an initial nucleic acid template refers to purified or non-purified nucleic acid in a sample containing or suspected of containing a target sequence. Thus, the process may employ, for example, DNA, RNA or DNA:RNA hybrid. The initial nucleic acid template is not limited to a DNA or RNA which is ultimately translated into a protein product, but may also include non-coding nucleic acid or non-coding nucleic acid sequences located between coding sequences.

To substantially reduce the possibility of non-specific priming events, the invention provides a blocking oligonucleotide which competes with non-specific priming sequences for hybridization to the primer. A blocking oligonucleotide of this invention is "incapable of acting as a primer for polymerase", i.e., not able to act as a point of initiation for extension product synthesis. A blocking oligonucleotide can be rendered incapable of acting as a primer for an extension reaction by removing or modifying the 3' terminal hydroxyl group, e.g., addition of a terminal 3'-dideoxynucleotide, 3'-phosphorylation, 3'-amino termination and the conjugation of a bulky molecular moiety such as rhodamine at the vicinity of the 3' end to sterically hinder the polymerase from catalyzing the extension reaction. Representative conditions for extension product synthesis are provided in the Examples.

It is desirable in most situations in which the 3' terminal end of a primer protrudes or extends beyond its blocking oligonucleotide to precludes any unintended extension of the primer in a 5'→3' direction when it is hybridized to its blocking oligonucleotide in a "primer: blocking oligonucleotide duplex". In this context, it should be pointed out that the formation of a primer: blocking oligonucleotide duplex is a reversible process. Thus, under an appropriate condition (e.g., an increase in temperature followed by a reduction in temperature), the duplex may repeatedly dissociate and re-associate.

The term "blocking oligonucleotide" refers broadly to an oligonucleotide capable of hybridizing to a primer to prevent non-specific priming events. Since a blocking oligonucleotide has sufficient complementarity to its corresponding primer, at a proper concentration it can stabilize the primer not engaged in specific priming event and thus prevent nonspecific priming event. By "sufficient complementarity" is meant that the two sequences must have a degree of nucleotide complementarity sufficient for the hybridization to occur. Preferably, there is a blocking oligonucleotide for each primer at the outset of the amplification reaction.

It will be understood by one of ordinary skill in the art that for hybridization between two strands to occur degree of complementarity and concentration are interdependent variables. Thus, a blocking oligonucleotide may be perfectly complementary with its corresponding primer, or alternatively, imperfectly complementary with the primer, provided that the blocking oligonucleotide is present at a sufficient concentration to prevent binding of the primer to the nonspecific sequences. In general, a nucleic acid sample is double-stranded. It is therefore necessary to separate the strands prior to extension product synthesis. In the Examples provided below, heat denaturation was used to separate the strands of the nucleic acid sample. However, alternative agents are known in the art for separating nucleic acid strands, which include enzymatic agents such as RecBCD helicase. See Muskavitch et al. (1981, *Enzyme* 14:233, hereby incorporated by reference). The primer and its blocking oligonucleotide may be added as a duplex or as two separate entities to a nucleic acid sample. If a primer and its blocking oligonucleotide are added as a duplex, the steps taken to effect denaturation of the nucleic acid sample will likewise separate the primer:blocking oligonucleotide duplex into its respective strands.

Following strand separation, the reaction mixture is subjected to proper hybridization conditions to enhance hybridization of each primer to either its priming sequence of the template to form a primer:template complex or to a blocking oligonucleotide to form a primer:blocking oligonucleotide duplex. Proper hybridization conditions are well known in the art, and some of them can be found in the Examples below.

Once the primers are hybridized to the priming sequences of the template, the reaction mixture is subjected to proper extension reaction conditions to permit the primers to act as initial points of an extension reaction, i.e., a polymerization reaction. It is not required that hybridization of the primer to the template and extension of the primer proceed under two distinct reactions. Thus, hybridization and extension may proceed simultaneously by combining those conditions required for hybridization with those required for extension. Proper extension reaction conditions, which are well known in the art, are controlled conditions (e.g., temperature, pH and ionic strength) for inducing synthesis of an extension product at the 3' end of a primer hybridized to a nucleic acid template upon addition of nucleotides in the presence of a catalyst, e.g., DNA polymerase. Representative extension reaction conditions are also provided in the Examples below.

The catalyst for the extension reaction is generally a DNA polymerase, e.g., a thermostable polymerase such as *Thermus aquaticus* or *Thermus thermophilus* See, Kong et.al, *J. Biol. Chem.* (1993) 268:1965, hereby incorporated by reference. To practice this invention, it is critical that a polymerase is capable of carrying out the activity of displacing an oligonucleotide hybridized to the template "downstream" of the sequence to which a primer is hybridized. Under proper extension reaction conditions, the polymerase proceeds to sequentially add nucleotides to the 3' terminus of an extension primer, and displace a blocking oligonucleotide, if any, hybridized "downstream" to the primer, thereby synthesizing an extension product having a sequence which is complementary to the target sequence of the template and encompasses the sequence of the blocking oligonucleotide.

In the case of a double-stranded nucleic acid template, two extension products are initially synthesized, each extension product corresponding to one strand of the target sequence. The newly synthesized extension product not only represents a duplicate of the target sequence, but also includes the primer sequence, which may or may not contain a stretch of noncontiguous sequence. The newly synthesized extension products are then separated from the initial template strand and used as subsequent templates for synthesizing additional extension products. Thereafter, the segment of a primer which is noncontiguous to the priming sequence of the initial template, if any, is duplicated and integrated into the extension product. Note that each extension product, which can then be used as a template in the subsequent extension reaction, consists of two covalently linked parts: (i) the entirety of a primer including a noncontiguous segment, if any, and (ii) the amplified nucleic acid sequence complementary to a strand of the target sequence. Completion of strand separation, hybridization and extension/displacement constitutes one cycle of an amplification reaction. Thus, the concentration of the extension product increases at an exponential rate with the completion of increasing amplification cycles.

In a preferred embodiment, both a primer and its blocking oligonucleotide are labeled respectively with, for example, a donor fluorophore and an acceptor fluorophore, which are brought in close proximity through hybridization to allow resonance energy transfer. As extension proceeds, availability of the labeled primer decreases due to its being incorporated into extension product. This reduces the amount of the labeled primer available to be hybridized to the labeled blocking oligonucleotide. As extension proceeds in repeated cycles, unlabeled extension product capable of binding to the primer is manufactured, and competes with the labeled blocking oligonucleotide for hybridization with the primer. Thus, in this preferred embodiment, the blocking oligonucleotides serve a dual role: (1) as blocking molecules for eliminating or reducing nonspecific priming events, and (2) as signal probes participating in the detection process.

When fluorophores are used to practice this invention, two fluorophores, a donor and an acceptor, are attached to the blocking oligonucleotide and its corresponding primer, such that they are within resonant energy transfer distance of one another when the blocking oligonucleotide and the primer are hybridized to one another in duplex form. The fluorophores are preferably separated from one another by at least one nucleotide but by no more than 100 Å (Clegg, *Methods in Enzymology* 211:353). It is also preferred that the fluorophores be attached to internal nucleotides. If desired, more than two fluorophores can be used. Also note that the fluorophores can be the same or different. The overlap of emission spectrum of the donor fluorophore and the excitation spectrum of the acceptor fluorophore allows energy transfer between them. Accordingly, a change in signal due to disruption of the energy transfer is generated when a primer:blocking oligonucleotide duplex is denatured or dissociated, for example, during extension reaction.

If desired, a fluorophore labeled blocking oligonucleotide which is neither substantially complementary (i.e., a complementarity of at least 5 base pairings) to any primer nor to the target sequence of the initial template can be first prepared. A "universal detection duplex" is made of the blocking oligonucleotide and a second fluorophore labeled oligonucleotide, in which the blocking oligonucleotide is complementary to, and overhangs the 3' end of, the second oligonucleotide. Prior to admixing a specific primer with the initial template for extension reaction, the blocking oligonucleotide is brought to the primer's complementarity through a ligation process, wherein the 3' end of the second oligonucleotide is covalently attached to the 5' end of the primer. In other words, the term "universal detection duplex" is used to describe an oligonucleotide formed between a blocking oligonucleotide and its complementary oligonucleotide which does not serve as a primer. For obvious reasons, the two fluorophores (or more) of the universal detection duplex must be in close proximity. In a particularly preferred embodiment, a donor fluorophore and an acceptor fluorophore are attached to the respective oligonucleotides of a universal detection duplex of weak stability, and subsequent ligation of the primer to the duplex gives a more stable duplex-primer. As a result, the energy transfer efficiency between the two fluorophores is enhanced.

Unlike a universal detection duplex, a "specific detection duplex" is ready for use in the amplification/detection of a target nucleic acid. See FIG. 1. The solid circle and solid square stand for two fluorophores and the hollow circle stands for an incapacitated 3' end of the blocking oligonucleotide. Note that in the embodiment shown in FIG. 1, the labeled primer contains a segment noncontiguous to its priming sequence. Further, a pre-asymmetric amplification, which preferentially amplifies the strand to which the labeled primer binds, is conducted to enhance both the sensitivity and selectivity. An asymmetric reaction can be induced by providing unequal amounts of the primers, i.e., an excessive one and a limiting one, or by providing primers of unequal lengths in complementarity to the specific priming sequence. Other factors may also contribute to the asymmetric nature of amplification, such as the difference in rate for the synthesis of each template strand. The optimal primer ratio for asymmetric amplification is a factor to be determined empirically. See Shyamala et al., 1989, *J. Bacteriol.* 171:1602, hereby incorporated by reference.

Figure 2:
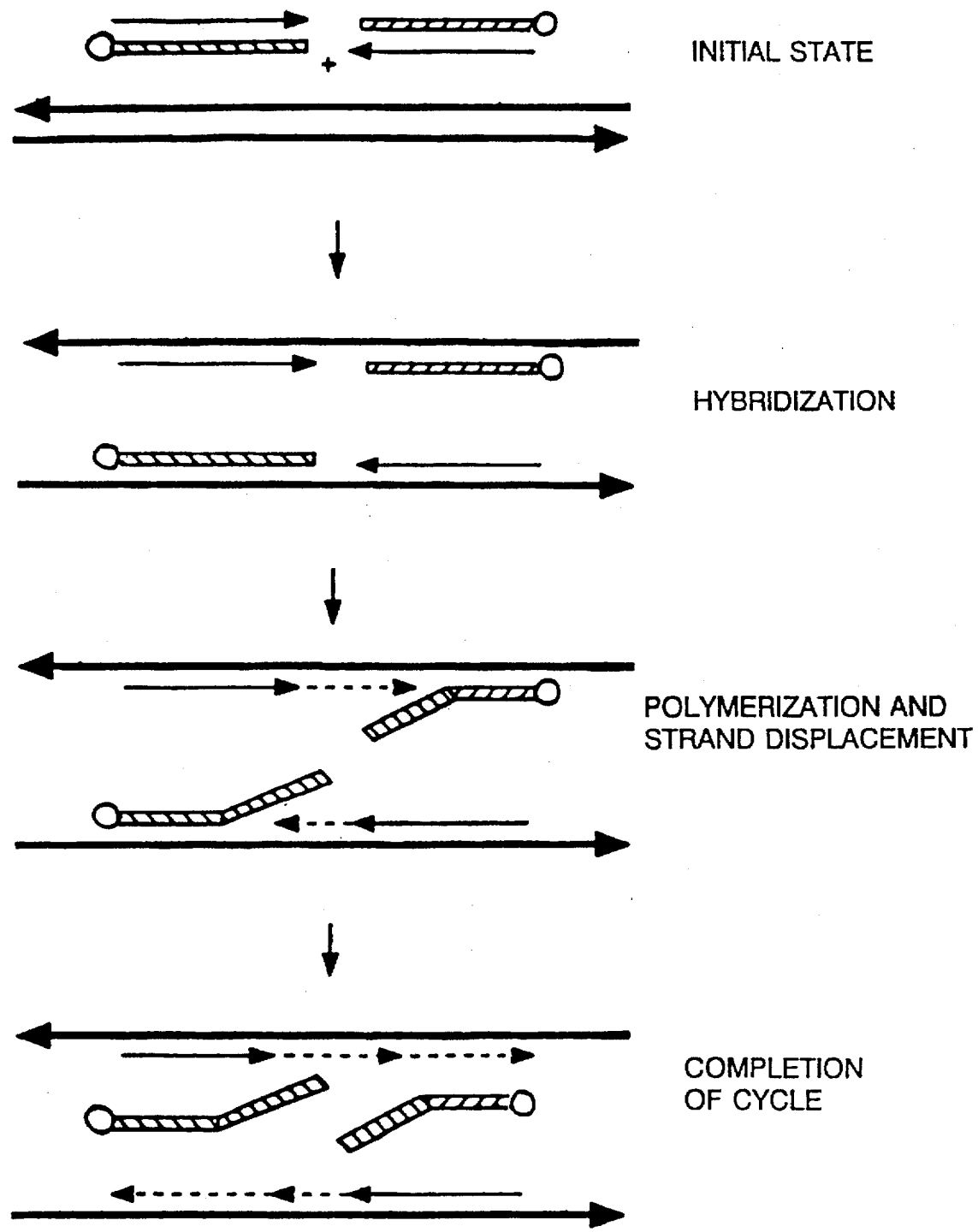
FIG. 2 is another embodiment of the method of this invention.

Another type of a "specific detection duplex" is used in the method shown in FIG. 2. In this embodiment, two unlabeled specific detection duplexes (i.e., two blocking oligonucleotide:primer pairs) are used. Neither primer has a segment which is not contiguous to its priming sequence. Again, each hollow circle stand for an incapacitated 3' end of a blocking oligonucleotide. Of note, the important process of displacing downstream blocking oligonucleotides is depicted in this figure, which is not shown in FIG. 1.

The method of this invention can be carried out in an apparatus for simultaneously performing amplification of a target sequence in a nucleic acid template and detecting the presence of the amplified target without conducting a separation step. The apparatus includes (1) an oligonucleotide container for containing oligonucleotides; (2) a reaction vessel for containing a nucleic acid sample, wherein the vessel is operatively linked to the oligonucleotide container to permit automated transfer of the contents of the oligonucleotide container to the reaction vessel; (3) a controller for mixing the oligonucleotides and the sample; (4) a temperature controller for controlling the temperature of the reaction vessel; (5) an irradiation source; and (6) a detector for detecting radiation emitted from the reaction vessel. Preferably, the reaction vessel is a well of a multi-well microtiter plate. Generally, the irradiation source is a device capable of generating photons of a desired wavelength. Such a device is well known to those of ordinary skill in the art, and indeed is commercially available (e.g., tungsten lamps or ionizing laser lamps). The detector is a device capable of converting photon energy into an electrical signal. Again, such a device is well known and can be obtained from numerous suppliers. Examples include photomultiplier tubes and semiconductor-based photon detectors.

It is particularly preferred that the apparatus further include a data processor for processing the signal data received by the detector. The apparatus can include a control mechanism which terminates the amplification reaction when a pre-designated level of radiation, corresponding to a pre-selected level of amplification, is detected by the detector. Thus, the apparatus provides for "on-line" monitoring of the amplification reaction in a manner analogous to the on-line monitoring of fermentation products used for large scale recombinant protein synthesis. Accordingly, use of the homogeneous amplification and detection method in combination with the apparatus disclosed herein eliminates contamination of the reaction vessel by eliminating the need to sample the mixture to determine the degree to which target sequence amplification has occurred.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever.

EXAMPLE I

Effect of a Blocking Oligonucleotide on Reducing Nonspecific Priming Events

To illustrate the effect of a blocking oligonucleotide on priming efficiency, a 127 bp segment of human SRY gene (Sinclair et al., 1990, Nature 346: 240, hereby incorporated by reference) was amplified in the presence or absence of a blocking oligonucleotide. The sequence of the target defining primers are primer (A) 5'-AACTC AGAGA TCAGC AAGCA GCTGG GATAC-3' (SEQ ID NO:1) and primer (B) 5'-ACTTA TAATT$_{TR}$ CGGGT ATTTC T$_{TR}$CTCT GTGCA-3' (SEQ ID NO:2). Each T$_{TR}$ stands for a Texas Red conjugated Amino-C6-dT residue (Glenn Research, Sterling, Va.) and was conjugated to Primer(B) following the procedures suggested by the supplier (Molecular Probes, Inc. Eugene, Oreg. U.S.A.). The blocking oligonucleotide used is complementary to 24 bases of primer (A) and has a sequence of 5'-CAGCT GCTTG CTGAT CTCTG AGTTL-3' (SEQ ID NO:3), in which "L" indicates a 3'-amine termination (3'-Amine-ON CPG, Clontech, Palo Alto, Calif.).

All of the oligonucleotides were synthesized by Operon Technologies, Inc. (Alameda, Calif.) and subsequently purified by electrophoresis on an 8M urea/15% acrylamide gel. The specific bands of the oligonucleotides were electrophoretically eluted and quantified by UV absorbance at 260 nm.

Male human genomic DNA, which was used as target DNA, was extracted from whole blood by the DTAB/CTAB method (Gustinicich et al., 1991, Biotechniques 11:298, hereby incorporated by reference), quantified by UV 260 nm absorbance, and serially diluted in TE buffer (10 mM Tris-HCl and 1 mM EDTA, pH 8.0) with 50 ng/μl yeast tRNA as carrier.

Amplification was carried out in a 96 well polycarbonate microtiter plate (Costar, Cambridge, Mass.) using an AG-9600 Thermal Station (MJ Research, Watertown, Mass.). To a 10 μl reaction of 50 mM Tris-HCl, pH 8.7, 40 mM KCl, 5 mM NH$_4$Cl, 2 mM DTT, 0.1% Triton X-100, 100 μM dNTP with 0.3 Unit of Tth DNA polymerase (Carballeira et al., 1990, Biotechniques 9: 276, hereby incorporated by reference) and varying amounts of target DNA ($10^2$, $10^3$ and $10^4$), 30 ng each of the primers with or without an equal amount of blocking oligonucleotide were added. Both yeast tRNA and salmon sperm DNA were used as negative controls. A total of 35 thermal cycles (94° C. for 25 seconds, 60° C. for 20 seconds and 72° C. for 40 seconds) was performed prior to analyzing the samples on a 9% acrylamide gel electrophoresized in TBE buffer at 10 V/cm. The molecular marker used for gel electrophoresis was the HpaII digestion of pBR322 DNA. The gel was stained briefly with ethidium bromide and photographed under UV illumination. The photograph is shown in FIG. 3.

Figure 3:
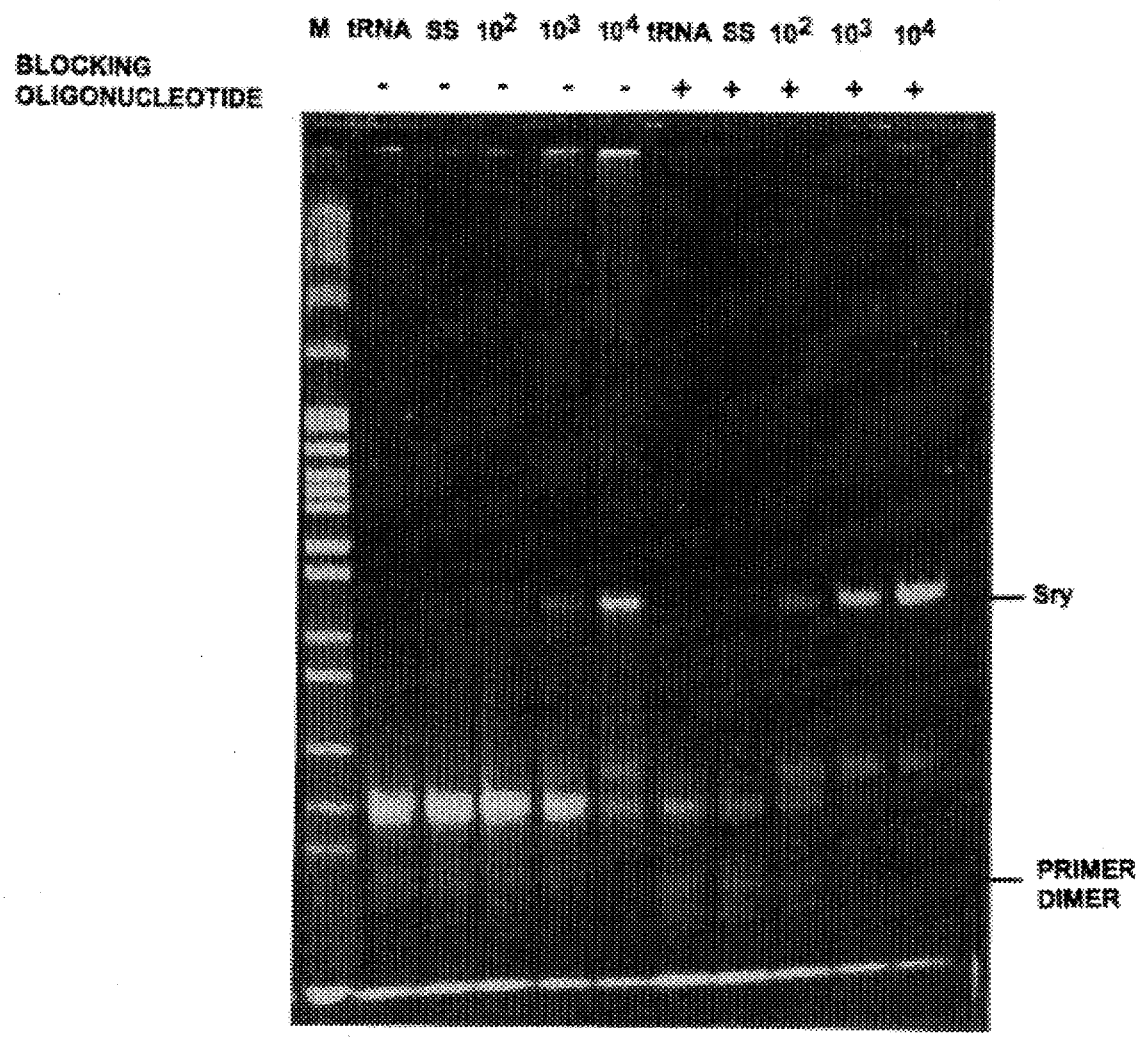
FIG. 3 is a photograph of a gel showing the effect of a blocking oligonucleotide on reducing nonspecific priming events.

Referring to FIG. 3, the content of each lane of the gel is indicated, in which tRNA stands for yeast transfer RNA, SS stands for salmon sperm DNA, M stands for molecular size marker, and the numbers stand for the amounts of target molecules. Symbol "−" or "+" represents the absence or presence of the blocking oligonucleotide. The intensity of 127 bp SRY specific sequence was more prominent for reactions with the presence of the blocking oligonucleotide, more so at lower target dosages. On the contrary, the intensity of the primer dimer was more conspicuous for reactions in the absence of the blocking oligonucleotide. The amplification efficiency of a specific target sequence was, therefore, directly affected by the extent of the interference from non-specific priming events such as formation of primer dimer, which was significantly more abundant in reactions without blocking oligonucleotides.

EXAMPLE II

Use of a Fluorophore Labeled Blocking Oligonucleotide to Monitor the Amplification of a Target Nucleic Acid This example illustrates that a blocking oligonucleotide not only can reduce nonspecific priming, but when labeled with a fluorophore, it can also be used to monitor the amplification process. The target DNA, the blocking oligonucleotide and the primers employed in this example are essentially the same as that used in Example I, except that, an indicator probe, which is complementary to 20 bases of primer (B) and has the sequence of 5'-AGAGA GAAAT ACCCG AATTAL-3' (SEQ ID NO:4), was included to participate in the fluorescence energy transfer with primer (B). "L" indicates a 3'-amine termination (3'-Amine-ON CPG, Clontech, Palo Alto, Calif.). After purification, the indicator probe was further conjugated with Fluorescein following the procedures suggested by the supplier (Molecular Probes, Inc. Eugene, Oreg. U.S.A.).

Amplification was carried out in a 96 well polycarbonate microtiter plate (Techne Inc., Cambridge, England) using an MW-1 Thermocycler (Techne Inc., Cambridge, England). To a 20 μl reaction of 50 mM Tris-HCl, pH 8.7, 40 mM KCl, 5 mM NH$_4$Cl, 2 mM DTT, 0.1% Triton X-100, 100 μM dNTP with 0.6 Unit of Tth DNA polymerase and $10^2$ copies of target DNA, 20 ng each of the primers with or without equal amount of blocking oligonucleotide were added. Salmon sperm DNA were used as negative controls. A total of 24 thermal cycles (96° C. for 42 seconds, 53° C. for 42 seconds and 72° C. for 60 seconds) was performed prior to adding the indicator probe to each reaction. An initial 630 nm fluorescence reading for each reaction was taken at cycle 25 using a microplate fluorimeter (Model 7600, Cambridge Technologies, Inc., Watertown, Mass., U.S.A.). Subsequent readings were taken at cycle 30 and cycle 35. The fluorescence readouts were plotted and presented in FIG. 4.

Figure 4:
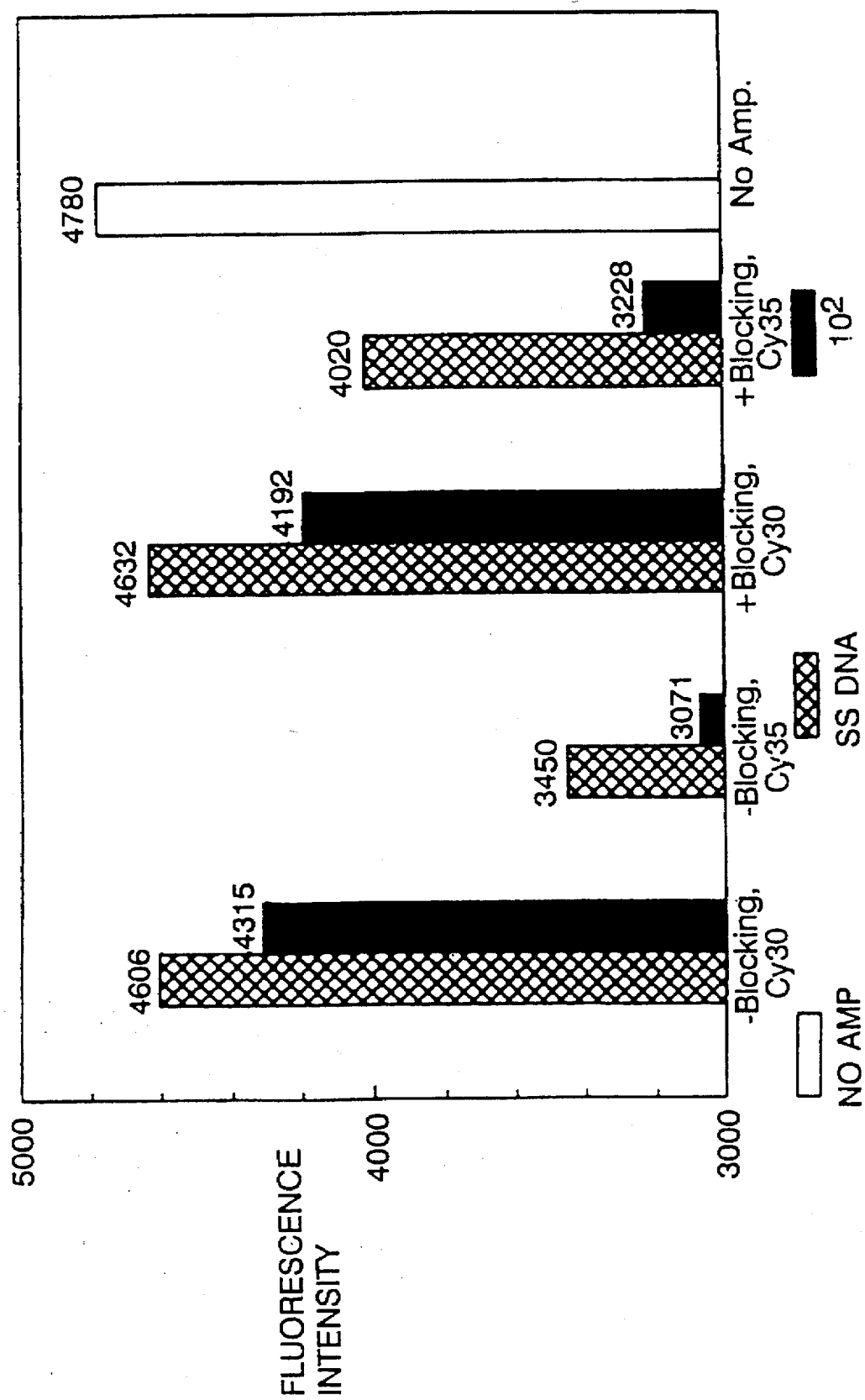
FIG. 4 is a graph showing the use of a fluorophore labeled blocking oligonucleotide to monitor specific priming events.

The bar-graph in FIG. 4 illustrates the extent of fluorescence signal change at two different cycles in amplification carried out with or without the initial addition of the blocking oligonucleotide. The decrease of fluorescence signal is an indication of the dissociation of the primer:blocking oligonucleotide duplex, which, in the absence of non-specific priming events, is proportional to the extent of primer incorporation into the amplified target sequence. Reaction without Tth DNA polymerase was used as the control of fluorescence signal (marked as "No Amp"). Samples containing $10^2$ copies SRY sequence and salmon sperm DNA were assayed in parallel to observe the target specific and non-specific signals. As shown in the figure, in the late amplification phase (cycle 35), the presence of the blocking oligonucleotide reduced non-specific priming events as evidenced by the difference in the fluorescence change between the two salmon sperm DNA controls in which the blocking oligonucleotide was absent and present, respectively.

EXAMPLE III

Enhancement of Energy Transfer through Ligation of a Universal Detection Duplex with a Primer In this example, two sets of universal oligonucleotides were used to illustrate the energy transfer enhancement induced by a ligation process in which the complementary oligonucleotide is ligated to a primer with its blocking oligonucleotide as the template.

All oligonucleotides were synthesized, purified and conjugated to the fluorophores according to procedures described in previous examples. For the ligation reaction, 200 ng of the blocking oligonucleotide along with equal molar amounts of its complementary oligonucleotide and a primer were added into a 20 μl reaction mixture containing 0.15 Unit of T4 DNA ligase (New England Biolab, Beverly, Mass.), 0.5 Unit of T4 polynucleotide Kinase (New England Biolab, Beverly, Mass.), 1 mM ATP and buffer (70 mM Tris HCl pH=7.6, 10 mM $MgCl_2$ and 5 mM DTT). Ligation reactions were carried out in duplicate by incubating at 40° C. for 1 hour and 30 minutes, and the reaction was terminated by heating at 95° C. for 10 minutes. Both prior and after each reaction, an aliquot of the reaction mixture was measured for its fluorescence intensity at emission of 630 nm with 495 nm excitation.

SET A: The blocking oligonucleotide has a sequence of 5'-$T_{TR}$TTTT GAACA GGCCT TGT$_{TR}$G-3' (SEQ ID NO:5), its complementary oligonucleotide has a sequence of 5'-CAAGG CCT$_F$G-3', and the primer has a sequence of 5'-TTCAA <u>ACCTGTGCTT AGGGC ACTG</u>-3' (SEQ ID NO:6) with the bases complementary to the priming sequence underlined. $T_{TR}$ stands for Texas Red conjugated Amino-C6-dT residue and $T_F$ stands for fluorescein conjugated amino-C6-dT residue. For their attachment to the oligonucleotides, see Examples I and II above.

The fluorescence reading of the reaction mixture prior to ligation was 900±23, and the reading after the ligation was 1336±211. Thus the ligation induced energy transfer in set A was 1.48 fold.

SET B: The blocking oligonucleotide has a sequence of 5'-$T_{TR}$TGGT CTCGA CCTCC TTGT$_{TR}$G-3' (SEQ ID NO:7); its complementary oligonucleotide has a sequence of 5'-CAAGG AGGT$_F$C G-3' (SEQ ID NO:8); and the primer has a sequence of 5'-AGACC <u>ACCTG TGCTT AGGGC ACTG</u>-3' (SEQ ID NO:9) with the bases complementary to the priming sequences underlined.

The fluorescence reading of the reaction mixture prior to ligation was 1489±58, and the reading after the ligation was 3019±94. Thus the ligation induced energy transfer in set B was 2.03 folds.

EXAMPLE IV

Application of a Detection Duplex to Monitor the Asymmetric Amplification of a Target Nucleic Acids.

To demonstrate the application of a detection duplex, we used either (A) a primer:blocking oligonucleotide duplex, or (B) a universal detection duplex coupled to a primer to monitor the amplification process. For duplex (A), the blocking oligonucleotide is complementary to both the primer and the initial target sequence. For duplex (B), the primer was ligated to the complementary oligonucleotide of the blocking oligonucleotide to allow the establishment of complementarity between the primer and blocking oligonucleotide. Both duplexes (A) and (B) were applied to the same amplification reactions. Segments of human acute myeloid leukemia breakpoint related sequence (AML-1) and human X-chromosome specific ameloginen (AMG-X) were used as the amplification targets to illustrate the application. Preparation of the primer:blocking oligonucleotide duplex Duplex (A): The sequences of the primer and the blocking oligonucleotide used for AML-1 are 5'-ACGGG GA<u>T</u>AC GCATC ACAAC AA-3' (SEQ ID NO:10) and 5'-<u>T</u>TGAT GCGTA TCCCC GT<u>T</u>T-3' (SEQ ID NO:11), respectively, and those used for AMG-X are 5'-AGACT GAG<u>T</u>C AGAGT GGCCA GGC-3' (SEQ ID NO:12) and 5'-<u>T</u>CCAC TCTGA CTCAG TC<u>T</u>TA-3' (SEQ ID NO:13), respectively. The primers and blocking oligonucleotides were conjugated with fluorescein and Texas Red, respectively, at the underlined positions. The 3' termini of the blocking oligonucleotides was incapacitated for extension by 3'-dideoxy termination.

Duplex (B): the primer for AML-1 has a sequence of 5'-<u>GGGAC GCACG</u> GGGAA ACGCA TCACA ACAA-3' (SEQ ID NO:14) and the primer for AMG-X has a sequence of 5'-GGGAC GCAGA CTGAG TCAGA GTGGC CAGGC-3' (SEQ ID NO:15); in each sequence, the bases complementary to one strand of Duplex (B) are underlined. Duplex (B), to which each primer was ligated, consists of the following two strands: 5'-GCGT$_{TR}$C CCATC TAGAT GGCCl$_{TR}$-3' (SEQ ID NO:16) and 5'-GGCCA TCT$_F$AG AT-3' (SEQ ID NO:17). The enhancement of energy transfer for AML-1 primer and AMG-X primer were 2.62 and 2.42 folds, respectively, upon ligation.

Asymmetric amplification and detection

For the AML-1 target, the excess primer is 5'-TGTTT GCAGG GTCCT AACTC AATCG-3' (SEQ ID NO:18), the limiting primer is 5'-GCGGC GTGAA GCGGC GGCTC G-3' (SEQ ID NO:19); and for AMG-X target, the excess primer is 5'-TGATG GTTGG CCTCA AGCCT GTG-3' (SEQ ID NO:20), the limiting primer is 5'-TGGGA TAGAA CCAAG CTGGT CAG-3' (SEQ ID NO:21).

Male human genomic DNA used as target was extracted from whole blood by methods according to Example I.

The target sequences were asymmetrically amplified for 20 cycles prior to the addition of the primer duplex. The asymmetric amplification was performed with excess primer to limiting primer ratio of 7.5 (1.2 µM vs 0.16 µM) in a 10 µl reaction containing 1 Unit of Tth DNA Polymerase, 50 mM Tris HCl, 40 mM KCl, 5 mM $NH_4Cl$, 100 µM dNTP, 5 mM $MgCl_2$ and 0.1% Triton X-100. Cycling conditions are identical to that used in Example I. The reactions were carried out in a 96-well polycarbonate microplate (Costar, Cambridge, Mass.) on a AG-9600 Silver Block Thermal Station (MJ Research, Watertown, Mass.).

4 ng each of the primer duplexes were added to the reaction well at room temperature to initiate the concomitant amplification and signal detection. As the baseline of calibration, the initial 630 nm fluorescence emission was measured at cycle 21 using 485 nm excitation. Subsequent signal measurement was taken at cycle 28 and every other cycles thereafter.

Figure 5:
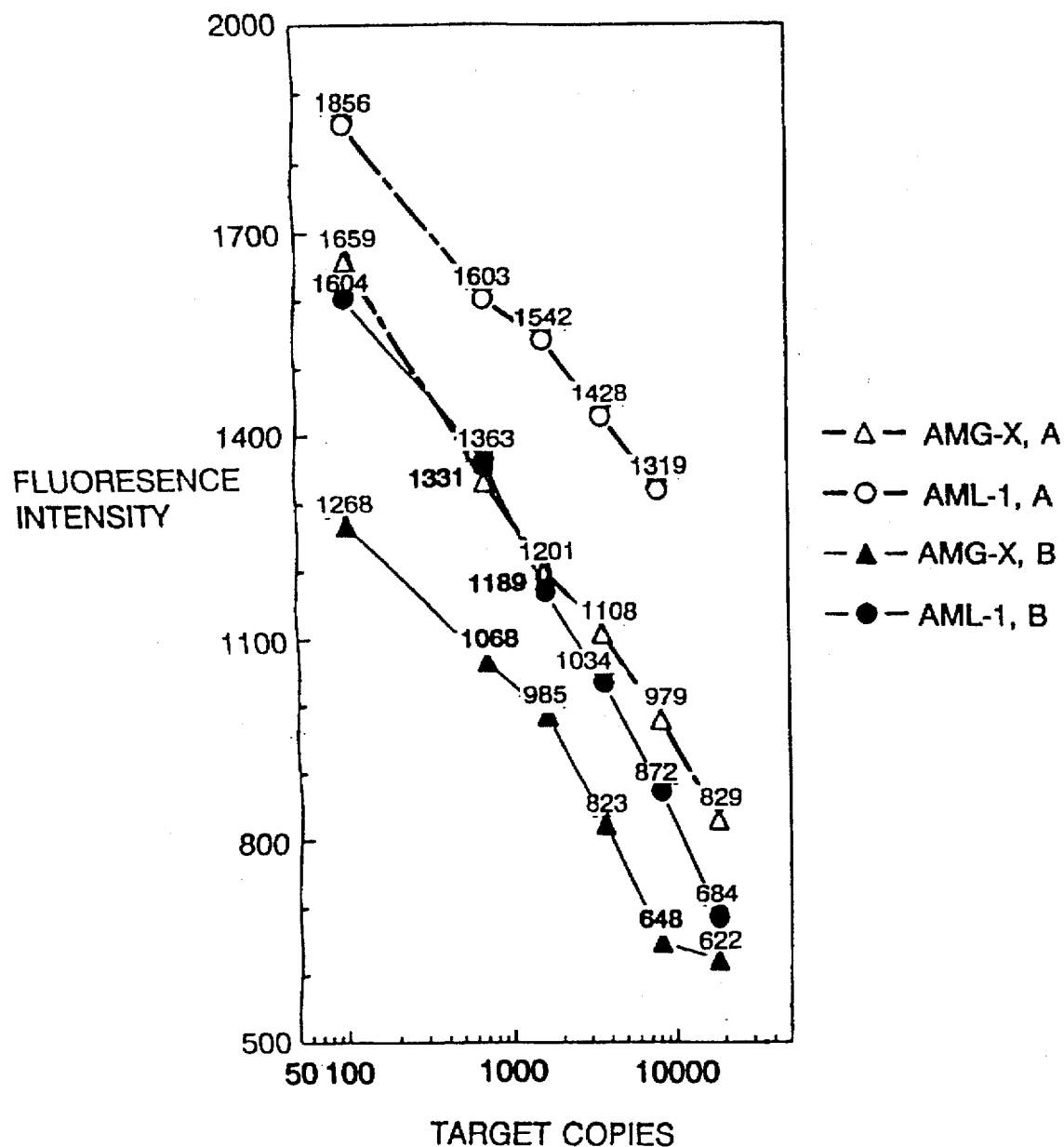
FIG. 5 is a graph showing the resolution and sensitivity in the detection of two different target sequences using two probes embodied by this invention.

The results compiled from detection at cycle 30 is illustrated in FIG. 5, which demonstrated the quantitative resolution and detection sensitivity by duplexes (A) and (B). As shown in the figure, the decrease in fluorescence intensity reflects the initial target doses.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

We claim:

1. A kit for detecting a target nucleic acid, said kit comprising:

a first primer with or without a segment noncontiguous to a first priming sequence, and a second primer with or without a segment noncontiguous to a second priming sequence, which said first and second primers are to be used with a polymerase for the amplification of the target nucleic acid; and an oligonucleotide which is incapable of acting as a primer for said polymerase and has at least 5 consecutive nucleotides fully complementary to at least 5 consecutive nucleotides of said first primer; wherein each of said first primer, said second primer and said oligonucleotide contains 10–50 nucleotides.

2. The kit of claim 1, wherein said first primer and said oligonucleotide are provided as a duplex.

3. The kit of claim 1, wherein said oligonucleotide has at least 8 consecutive nucleotides fully complementary to at least 8 consecutive nucleotides of said first primer.

4. The kit of claim 3, wherein each of said first primer, said second primer and said oligonucleotide contains 5–40 nucleotides.

5. The kit of claim 3, further comprising a polymerase.

6. The kit of claim 3, further comprising an additional oligonucleotide which is incapable of acting as a primer for said polymerase, contains 10–50 nucleotides, and has at least 8 consecutive nucleotides fully complementary to at least 8 consecutive nucleotides of said second primer.

7. The kit of claim 3, wherein a first fluorophore is covalently attached to said first primer and a second fluorophore is covalently attached to said oligonucleotide, with one of said two fluorophores being a donor fluorophore and the other being an acceptor fluorophore, so that when said first primer and said oligonucleotide are hybridized, said donor fluorophore and said acceptor fluorophore are in close proximity to allow resonance energy transfer therebetween.

8. A kit for detecting a target nucleic acid, said kit comprising:

a first oligonucleotide containing 10–50 nucleotides with a first fluorophore covalently attached thereto, said first oligonucleotide being incapable of acting as a primer for use with a polymerase in the amplification of a target nucleic acid; and a second oligonucleotide containing 5–30 nucleotides with a second fluorophore covalently attached thereto, said second oligonucleotide having a free 3' OH and being capable of hybridizing, via at least 5 consecutive fully complementary nucleotide pairings, with said first oligonucleotide; wherein said first oligonucleotide has an overhang beyond the 3' end of said second oligonucleotide by 1–12 nucleotides, and further, said first and second fluorophores, one of which is a donor fluorophore and the other an acceptor fluorophore, being in close proximity when said first oligonucleotide hybridizes to said second oligonucleotide to allow resonance energy transfer therebetween.

9. The kit of claim 8, wherein said first oligonucleotide contains 15–40 nucleotides and has an overhang beyond the 3' end of second oligonucleotide by 4–8 nucleotides, and said second oligonucleotide contains 7–15 nucleotides and is capable of hybridizing, via at least 8 consecutive fully complementary nucleotide pairings, with said first oligonucleotide.

10. The kit of claim 9, wherein said first and second oligonucleotides are provided as a duplex.

11. The kit of claim 9, further comprising a ligase.

12. The kit of claim 9, further comprising a kinase or a polymerase having 5'→3' exonuclease activity.

13. The kit of claim 11, further comprising a kinase or a polymerase having 5'→3' exonuclease activity.

14. The kit of claim 9, further comprising a polymerase with or without 5'→3' exonuclease activity.

15. A DNA duplex comprising:
- a first oligonucleotide which is capable of acting as a primer, with or without a segment noncontiguous to its priming sequence, for use with a polymerase in the amplification of a target nucleic acid;
- a second oligonucleotide which is hybridized, via at least 5 consecutive fully complementary nucleotide pairings, with said first oligonucleotide, said second oligonucleotide being incapable of acting as a primer for said polymerase; and
- a first fluorophore covalently attached to said first oligonucleotide and a second fluorophore covalently attached to said second oligonucleotide, with one of the said two fluorophores being a donor fluorophore and the other being an acceptor fluorophore, so that when said two fluorophores are in close proximity resonance energy transfer therebetween is allowed; wherein each of said first oligonucleotide and said second oligonucleotide contains 10–50 nucleotides.

16. The DNA duplex of claim 15, wherein each of said first oligonucleotide and said second oligonucleotide contains 15–40 nucleotides, and said second oligonucleotide is hybridized, via at least 8 consecutive fully complementary nucleotide pairings, with said first oligonucleotide.

17. A composition comprising:
- a first single-stranded oligonucleotide containing 10–50 nucleotides, said oligonucleotide being incapable of acting as a primer for use with a polymerase in the amplification of a target nucleic acid;
- a first fluorophore covalently attached to said oligonucleotide;
- a second single-stranded oligonucleotide containing 5–30 nucleotides, and having a free 3' OH, said second oligonucleotide being hybridized, via at least 5 consecutive fully complementary nucleotide pairings, with said first oligonucleotide and said first oligonucleotide overhanging the 3' end of said second oligonucleotide by 1–12 nucleotides;
- a second fluorophore covalently attached to said second oligonucleotide, said first and second fluorophores, one of which is a donor fluorophore and the other an acceptor fluorophore, being in close proximity to allow resonance energy transfer therebetween.

18. The composition of claim 17, wherein said first oligonucleotide contains 15–40 nucleotides and overhangs the 3' end of said second oligonucleotide by 4–8 nucleotides, and said second oligonucleotide contains 7–15 nucleotides and is hybridized, via at least 8 consecutive fully complementary nucleotide pairings, with said first oligonucleotide.

* * * * *

SEQUENCE LISTING ( 1 ) GENERAL INFORMATION:

( i i i ) NUMBER OF SEQUENCES: 21

( 2 ) INFORMATION FOR SEQ ID NO: 1:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 1:

AACTCAGAGA TCAGCAAGCA GCTGGGATAC            30

( 2 ) INFORMATION FOR SEQ ID NO: 2:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 2:

ACTTATAATT CGGGTATTTC TCTCTGTGCA            30

( 2 ) INFORMATION FOR SEQ ID NO: 3:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CAGCTGCTTG CTGATCTCTG AGTT            24

( 2 ) INFORMATION FOR SEQ ID NO: 4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( x i ) SEQUENCE DESCRIPTION: SEQ ID NO: 4:

AGAGAGAAAT ACCCGAATTA            20

( 2 ) INFORMATION FOR SEQ ID NO: 5:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TTTTTGAACA GGCCTTGTG            19

( 2 ) INFORMATION FOR SEQ ID NO: 6:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear (x i) SEQUENCE DESCRIPTION: SEQ ID NO: 6:

TTCAAACCTG TGCTTAGGGC ACTG                                                    24

(2) INFORMATION FOR SEQ ID NO: 7:

(i) SEQUENCE CHARACTERISTICS:
  (A) LENGTH: 20
  (B) TYPE: nucleic acid
  (C) STRANDEDNESS: single
  (D) TOPOLOGY: linear (x i) SEQUENCE DESCRIPTION: SEQ ID NO: 7:

TTGGTCTCGA CCTCCTTGTG                                                         20

(2) INFORMATION FOR SEQ ID NO: 8:

(i) SEQUENCE CHARACTERISTICS:
  (A) LENGTH: 11
  (B) TYPE: nucleic acid
  (C) STRANDEDNESS: single
  (D) TOPOLOGY: linear (x i) SEQUENCE DESCRIPTION: SEQ ID NO: 8:

CAAGGAGGTC G                                                                  11

(2) INFORMATION FOR SEQ ID NO: 9:

(i) SEQUENCE CHARACTERISTICS:
  (A) LENGTH: 24
  (B) TYPE: nucleic acid
  (C) STRANDEDNESS: single
  (D) TOPOLOGY: linear (x i) SEQUENCE DESCRIPTION: SEQ ID NO: 9:

AGACCACCTG TGCTTAGGGC ACTG                                                    24

(2) INFORMATION FOR SEQ ID NO: 10:

(i) SEQUENCE CHARACTERISTICS:
  (A) LENGTH: 22
  (B) TYPE: nucleic acid
  (C) STRANDEDNESS: single
  (D) TOPOLOGY: linear (x i) SEQUENCE DESCRIPTION: SEQ ID NO: 10:

ACGGGGATAC GCATCACAAC AA                                                      22

(2) INFORMATION FOR SEQ ID NO: 11:

(i) SEQUENCE CHARACTERISTICS:
  (A) LENGTH: 19
  (B) TYPE: nucleic acid
  (C) STRANDEDNESS: single
  (D) TOPOLOGY: linear (x i) SEQUENCE DESCRIPTION: SEQ ID NO: 11:

TTGATGCGTA TCCCCGTTT                                                          19

(2) INFORMATION FOR SEQ ID NO: 12:

(i) SEQUENCE CHARACTERISTICS:
  (A) LENGTH: 23
  (B) TYPE: nucleic acid
  (C) STRANDEDNESS: single
  (D) TOPOLOGY: linear (x i) SEQUENCE DESCRIPTION: SEQ ID NO: 12:

AGACTGAGTC AGAGTGGCCA GGC                                                    23

(2) INFORMATION FOR SEQ ID NO: 13:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION: SEQ ID NO: 13:

TCCACTCTGA CTCAGTCTTA                                                        20

(2) INFORMATION FOR SEQ ID NO: 14:

(i) SEQUENCE CHARACTERISTICS:
        (A) LENGTH: 29
        (B) TYPE: nucleic acid
        (C) STRANDEDNESS: single
        (D) TOPOLOGY: linear (xi) SEQUENCE DESCRIPTION: SEQ ID NO: 14:

GGGACGCACG GGGAAACGCA TCACAACAA                                              29

(2) INFORMATION FOR SEQ ID NO: 15:

(i) SEQUENCE CHARACTERISTICS:
        (A) LENGTH: 30
        (B) TYPE: nucleic acid
        (C) STRANDEDNESS: single
        (D) TOPOLOGY: linear (xi) SEQUENCE DESCRIPTION: SEQ ID NO: 15:

GGGACGCAGA CTGAGTCAGA GTGGCCAGGC                                             30

(2) INFORMATION FOR SEQ ID NO: 16:

(i) SEQUENCE CHARACTERISTICS:
        (A) LENGTH: 19
        (B) TYPE: nucleic acid
        (C) STRANDEDNESS: single
        (D) TOPOLOGY: linear (xi) SEQUENCE DESCRIPTION: SEQ ID NO: 16:

GCGTCCCATC TAGATGGCC                                                         19

(2) INFORMATION FOR SEQ ID NO: 17:

(i) SEQUENCE CHARACTERISTICS:
        (A) LENGTH: 12
        (B) TYPE: nucleic acid
        (C) STRANDEDNESS: single
        (D) TOPOLOGY: linear (xi) SEQUENCE DESCRIPTION: SEQ ID NO: 17:

GGCCATCTAG AT                                                                12

(2) INFORMATION FOR SEQ ID NO: 18:

(i) SEQUENCE CHARACTERISTICS:
        (A) LENGTH: 25
        (B) TYPE: nucleic acid
        (C) STRANDEDNESS: single
        (D) TOPOLOGY: linear (xi) SEQUENCE DESCRIPTION: SEQ ID NO: 18:

TGTTTGCAGG GTCCTAACTC AATCG                                                  25

(2) INFORMATION FOR SEQ ID NO: 19:

(i) SEQUENCE CHARACTERISTICS:
        (A) LENGTH: 21
        (B) TYPE: nucleic acid
        (C) STRANDEDNESS: single
        (D) TOPOLOGY: linear (xi) SEQUENCE DESCRIPTION: SEQ ID NO: 19:

GCGGCGTGAA GCGGCGGCTC G        21

(2) INFORMATION FOR SEQ ID NO: 20:

(i) SEQUENCE CHARACTERISTICS:
        (A) LENGTH: 23
        (B) TYPE: nucleic acid
        (C) STRANDEDNESS: single
        (D) TOPOLOGY: linear (xi) SEQUENCE DESCRIPTION: SEQ ID NO: 20:

TGATGGTTGG CCTCAAGCCT GTG        23

(2) INFORMATION FOR SEQ ID NO: 21:

(i) SEQUENCE CHARACTERISTICS:
        (A) LENGTH: 23
        (B) TYPE: nucleic acid
        (C) STRANDEDNESS: single
        (D) TOPOLOGY: linear (xi) SEQUENCE DESCRIPTION: SEQ ID NO: 21:

TGGGATAGAA CCAAGCTGGT CAG        23